(12) United States Patent
Cheng et al.

(10) Patent No.: US 12,667,258 B2
(45) Date of Patent: Jun. 30, 2026

(54) SYSTEM OF MACHINE-LEARNING MEDIATED IMAGE ANALYSIS TO AID PREDICTIVE MRI-GUIDED HYPERTHERMIA TREATMENTS

(71) Applicant: ASTRID PHARMA CORP., Davis, CA (US)

(72) Inventors: R. Holland Cheng, Davis, CA (US); Mohammad A. Baikoghli, Davis, CA (US)

(73) Assignee: ASTRID PHARMA CORP, Davis, CA (US)

( * ) Notice: Subject to any disclaimer, the term of this patent is extended or adjusted under 35 U.S.C. 154(b) by 560 days.

(21) Appl. No.: 16/541,955

(22) Filed: Aug. 15, 2019

(65) Prior Publication Data

US 2020/0054216 A1 Feb. 20, 2020

Related U.S. Application Data

(60) Provisional application No. 62/719,082, filed on Aug. 16, 2018.

(51) Int. Cl.
A61B 5/00 (2006.01)
A61N 7/02 (2006.01)
(Continued)

(52) U.S. Cl.
CPC .......... A61B 5/0036 (2018.08); A61B 5/7267 (2013.01); A61B 5/745 (2013.01);
(Continued)

(58) Field of Classification Search
CPC ..... A61B 5/0036; A61B 5/055; A61B 5/7267; A61B 5/745; A61B 5/7485;
(Continued)

(56) References Cited

U.S. PATENT DOCUMENTS

| | | | | | |
|---|---|---|---|---|---|
| 5,224,492 | A | * | 7/1993 | Takahashi | A61B 5/417 607/105 |
| 2002/0177771 | A1 | * | 11/2002 | Guttman | G06T 15/08 600/410 |

(Continued)

OTHER PUBLICATIONS

Kalaiselvi et al. "Survey of using GPU CUDA programming model in medical image analysis", Aug. 6, 2017, Elsevier, Informatics in Medicine Unlocked 9, 133-144 (Year: 2017).*
(Continued)

*Primary Examiner* — Andrew W Begeman
(74) *Attorney, Agent, or Firm* — Haverstock & Owens, A Law Corporation

(57) ABSTRACT

A new generation of precision medicine with interfaces processing the predictive feedback over the course of hyperthermia treatment sessions is provided. Implementation of MR-thermometry measurements and real-time spatial imaging can resolve many of the limiting factors currently associated with hyperthermia treatment. More significantly, implementation of artificial intelligence (machine learning) mediated image analysis and database construction can provide the international community with standards for monitoring, and thermal dose calibration.

14 Claims, 7 Drawing Sheets

(51) Int. Cl.

| | |
|---|---|
| *G06T 7/00* | (2017.01) |
| *G16H 20/40* | (2018.01) |
| *G16H 30/20* | (2018.01) |
| *G16H 30/40* | (2018.01) |
| *G16H 50/20* | (2018.01) |
| *A61N 7/00* | (2006.01) |

(52) U.S. Cl.
CPC .............. *A61B 5/7485* (2013.01); *A61N 7/02* (2013.01); *G06T 7/0012* (2013.01); *G16H 20/40* (2018.01); *G16H 30/20* (2018.01); *G16H 30/40* (2018.01); *G16H 50/20* (2018.01); *A61B 2576/00* (2013.01); *A61N 2007/0004* (2013.01); *G06T 2200/24* (2013.01); *G06T 2207/10088* (2013.01); *G06T 2207/20081* (2013.01); *G06T 2207/30096* (2013.01)

(58) Field of Classification Search
CPC ................. A61B 2576/00; A61N 7/02; A61N 2007/0004; G06T 7/0012; G06T 2200/24; G06T 2207/10088; G06T 2207/20081; G06T 2207/30096; G16H 20/40; G16H 30/20; G16H 30/40; G16H 50/20
See application file for complete search history.

(56) References Cited

U.S. PATENT DOCUMENTS

| | | | | |
|---|---|---|---|---|
| 2013/0202173 A1* | 8/2013 | Buckler | ................. | G06T 7/143 |
| | | | | 382/131 |
| 2015/0038828 A1* | 2/2015 | Kohler | .............. | G01R 33/4804 |
| | | | | 600/412 |
| 2015/0038883 A1* | 2/2015 | Kurtz | ................ | G01R 33/4814 |
| | | | | 601/3 |
| 2015/0164432 A1* | 6/2015 | Gupta | ............... | A61B 5/14546 |
| | | | | 600/300 |
| 2017/0173365 A1* | 6/2017 | Bzdusek | ............... | G16H 70/20 |
| 2018/0264291 A1* | 9/2018 | Rem-Bronneberg | ........................ | |
| | | | | A61B 8/4488 |
| 2018/0322629 A1* | 11/2018 | Hu | ......................... | G06N 3/084 |
| 2021/0259775 A1* | 8/2021 | Kustra | ................ | A61B 5/4875 |

OTHER PUBLICATIONS

Stakhursky et al. "Real-time MRI-guided hyperthermia treatment using a fast adaptive algorithm", Apr. 7, 2009, Physics in Medicine and Biology, 2131-2145 (Year: 2009).*

Chen et al., "Chemically activatable viral capsid functionalized for cancer targeting", 2016, Nanomedicine, 11(4), 377-390 (Year: 2016).*

\* cited by examiner

SYSTEM OF MACHINE-LEARNING MEDIATED IMAGE ANALYSIS TO AID PREDICTIVE MRI-GUIDED HYPERTHERMIA TREATMENTS

CROSS-REFERENCE TO RELATED APPLICATIONS

The present application is related to and claims priority to U.S. Provisional Patent Application Ser. No. 62/719,082 filed on Aug. 16, 2018, which is hereby incorporated by reference in its entirety.

FIELD

The present invention relates to magnetic resonance imaging (MRI) guided hyperthermia treatment and, more particularly, to systems and methods of machine learning-mediated image analysis to aid predictive MRI-guided hyperthermia treatment.

BACKGROUND

Tumor (or cancer) is one of the common severe diseases of human beings, and is found to be one of the top three causes of death in many countries. Thus, tumor treatment is desperately called for in healthcare systems. Hyperthermia treatment (HT) has been proposed as tumor treatment. Hyperthermia treatment is achieved by detection of tumor, clinical analysis, and use of high-intensity focused ultrasound (HIFU) for treatment. HIFU is a non-invasive therapeutic technique that uses non-ionizing ultrasonic waves to heat tissue, and can be used to destroy tumors. HIFU may be combined with MRI technique to enable guidance of the treatment and monitoring. The aftermath of hyperthermia treatment planning is limited to pre- and post-treatment using MRI. Moreover, there is a lack of standardized HIFU calibration. Sensory parameters of temperature measurements and imaging-guidance are typically set by an operator, which can lead to insufficient care during treatment.

Currently, there is no standardized hyperthermia assessment for MRI-guided focused ultrasound treatment. Several factors, including biological, physical, and engineering components, are among the contributing factors that pose significant challenges for hyperthermia treatment planning. The variations caused by phenomena such as cavitation, blood flow, micro- and macroscopic calcification, standing waves, and beam penetration properties in soft vs. hard tissue, contribute greatly to such challenges, which may lead to difficulties in reaching effective thermal dose calibration and ultimately insufficiency during treatment.

It is in this context that various embodiments of the present invention arise.

SUMMARY

Implementation of MR-thermometry measurements and real-time spatial imaging is an obvious area of focus and can resolve many of the limiting factors currently associated with hyperthermia treatment. More significantly, implementation of artificial intelligence (machine learning) mediated image analysis and database construction can provide the international community with standards for monitoring, and thermal dose calibration. In order to prevent over-treating or under-treating the region of treatment, the present invention provides a real-time visualization system to enable accurate sensory assessment of both the temperature and the biological effect after each hyperthermia session, so that the treatment planning can be adjusted in timely manner to achieve precision hyperthermia with minimal negative impact to healthy tissue in the vicinity.

The present invention provides a system for performing MRI-guided hyperthermia treatment, comprising a magnetic resonance imaging (MRI) unit, a backend platform and a frontend platform. The MRI unit is configured to acquire MRI images from an imaging zone before, during and after a hyperthermia treatment, wherein the imaging zone includes a region of treatment (ROT).

The backend platform comprises a graphic processing unit (GPU), a computing unit and a database. The GPU is configured to receive and process the MRI images from the MRI unit and sensory data, and detect features of the ROT for the MRI images. The computing unit is configured to implement machine learning-aided analysis, which extracts information from the features of the ROT and the sensory data to train a predictive model. The predictive model generates, based on the MRI images and the sensory data, consecutive real-time visualization images of the ROT and thermal dose calibration during the hyperthermia treatment. The database is configured to store the MRI images, the sensory data, the real-time visualization images and the thermal dose calibration.

The frontend platform is configured to display the consecutive real-time visualization images and the thermal dose calibration to an operator, and allow the operator to operate the MRI-guided hyperthermia treatment. The frontend platform comprises a graphic user interface (GUI) and a controller. The GUI is configured to display the consecutive real-time visualization images and the thermal dose calibration to the operator. The controller is configured to receive a value of thermal dose inputted by the operator during hyperthermia treatment, and send the value of thermal dose to a treatment unit to control heating during the hyperthermia treatment.

In one embodiment, the predictive model had been pre-trained by prior MRI images and/or prior thermograms obtained before the hyperthermia treatment. The treatment unit comprises a high intensity focused ultrasound (HIFU) unit, which generates focused ultrasonic energy for sonicating the ROT during the hyperthermia treatment. The GPU comprises a high-throughput image processing GPU (HTIP-GPU). The features of the ROT are selected from the group consisting of morphological components and textural components. For example, the features of the ROT are selected from the group consisting of size, shape, texture, and a combination thereof. The sensory data is selected from the group consisting of regional temperature, thermal dose and biological effect. The consecutive real-time visualization images comprise consecutive 3D images. The database is further configured to store the value of thermal dose inputted by the operator.

The present invention also provides a method for performing MRI-guided hyperthermia treatment, comprising: acquiring MRI images from a imaging zone before, during and after a hyperthermia treatment, wherein the imaging zone includes a region of treatment (ROT); processing the MRI images and sensory data; detecting features of the ROT for the MRI images; extracting, by machine learning-aided analysis, information from the features of the ROT and the sensory data to train a predictive model; generating, by the predictive model, consecutive real-time visualization images of the ROT and thermal dose calibration during the hyperthermia treatment, based on the MRI images and the sensory data; displaying the consecutive real-time visualization images and the thermal dose calibration to an operator; and sending a value of thermal dose inputted by the operator to a treatment unit during the hyperthermia treatment, to control heating during the hyperthermia treatment.

In one embodiment, the method further comprises: pre-training, prior to the hyperthermia treatment, the predictive model by prior MRI images and/or prior thermograms obtained before the hyperthermia treatment; and/or storing the MRI images, the sensory data, the consecutive real-time visualization images and the thermal dose calibration. The method can further comprise: storing the value of thermal dose inputted by the operator. In another embodiment, the treatment unit comprises a HIFU unit, which generates focused ultrasonic energy for sonicating the ROT during the hyperthermia treatment. The step of processing the MRI images and sensory data is performed by an HTIP-GPU. The step of detecting features of the ROT for the MRI images is performed by an HTIP-GPU. The features of the ROT are selected from the group consisting of morphological components and textural components. The sensory data is selected from the group consisting of regional temperature, thermal dose and biological effect. The step of displaying the consecutive real-time visualization images comprises displaying consecutive 3D real-time visualization images.

These and other aspects are described further below with reference to the drawings.

DETAILED DESCRIPTION

Figure 1:
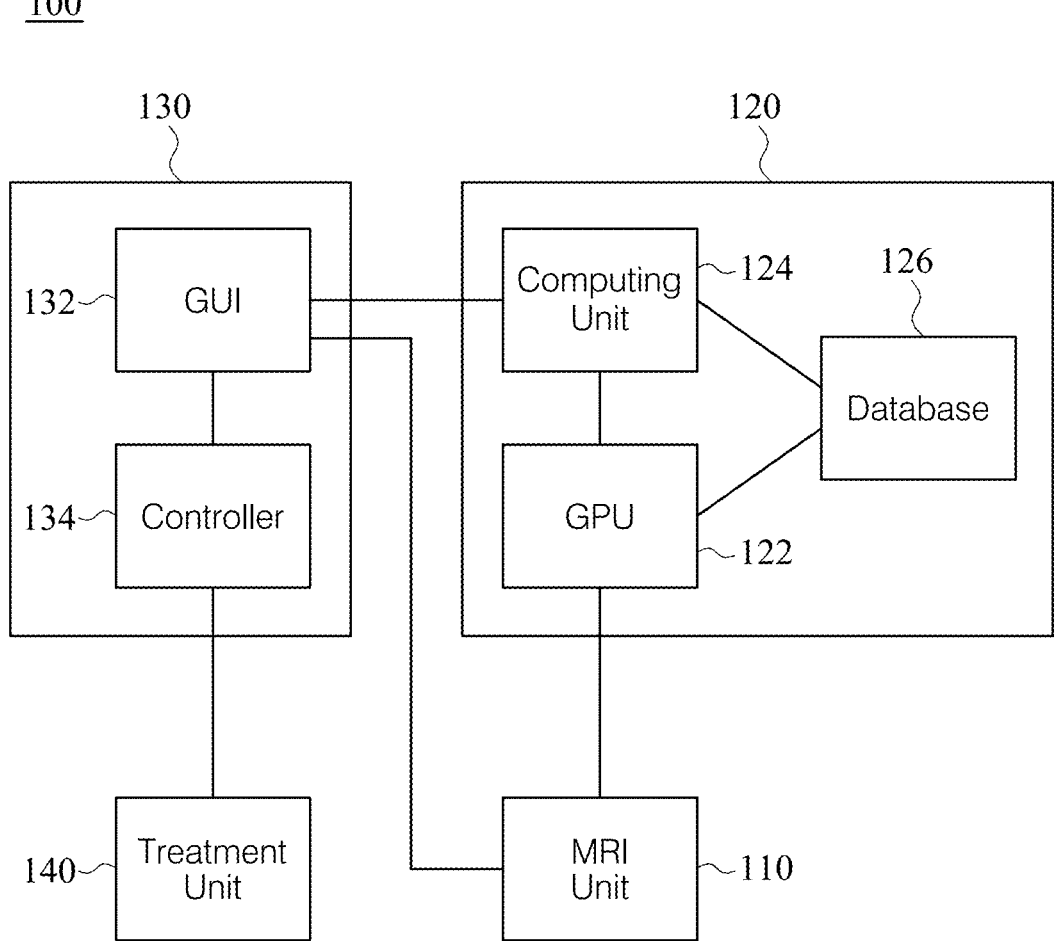
FIG. 1 is a schematic diagram of a system for performing MRI-guided hyperthermia treatment according to one embodiment of the present invention.

The objects, advantages and features of the present invention will become apparent from the following detailed descriptions in conjunction with the accompanying drawings.

In the following description, numerous specific details are set forth to provide a thorough understanding of the presented embodiments. The disclosed embodiments may be practiced without some or all of these specific details. In other instances, well-known structures and process operations have not been described in detail to not unnecessarily obscure the disclosed embodiments. While the present invention will be described in conjunction with the specific embodiments, it will be understood that the specific embodiments are not intended to limit the disclosed embodiments.

Furthermore, the various embodiments shown in the drawings are illustrative, and are not necessarily drawn to scale.

The present invention is to implement multi-parameter image processing, which entails image analysis and deep learning to aid high-throughput, predictive treatment planning during MRI-guided HIFU. The aim of the present invention is to provide a real-time feedback of integrated MRI and sensory data to the operator as a visual guide to ring HIFU engagement at the ROT, as well as subsequence ROTs. The sensory and graphical information during treatment can be utilized to design computer-aided predictive models to increase accuracy and success of the hyperthermia treatment.

The present invention provides physicians with standards for monitoring and thermal dose calibration, so that an urgent demand for machine learning-mediated image analysis and database construction is satisfied. In order to prevent over- or under-treatment to individual regions of treatment, the present invention provides and optimizes a real-time feedback system to enable accurate sensory assessment of both the temperature and the biological effect after each treatment (e.g. sonication) to adjust the treatment planning in time to achieve "precision hyperthermia" with minimal negative impact to healthy tissue in the vicinity.

FIG. 1 shows a schematic diagram of a system 100 for performing MRI-guided hyperthermia treatment according to one embodiment of the present invention. The system 100 comprises a magnetic resonance imaging (MRI) unit 110, a backend platform 120 and a frontend platform 130. The MRI unit 110 is configured to acquire MRI images from an imaging zone of a patient before, during and after a hyperthermia treatment. The imaging zone includes an ROT.

The backend platform 120 comprises a graphic processing unit (GPU) 122, a computing unit 124 and a database 126. The GPU 122 can receive and process the MRI images from the MRI unit 110 and sensory data, and detect features, such as morphological components and textural components, of the ROT for the MRI images. The computing unit 124 is configured to implement machine learning-aided analysis, which can extract information from the features of the ROT and the sensory data so as to train a predictive model. Based on the MRI images and the sensory data, the predictive model generates consecutive real-time visualization images of the ROT and thermal dose calibration during the hyperthermia treatment. The database 126 is configured to store the MRI images, the sensory data, the real-time visualization images and the thermal dose calibration.

In one embodiment, The GPU 122 is a high-throughput image processing GPU (HTIP-GPU), which can measure features of all MRI images to build a self-trained system. The sensory data is selected from the group consisting of regional temperature, thermal dose and biological effect. The consecutive real-time visualization images can be 2D and/or 3D images.

The frontend platform 130 can display the consecutive real-time visualization images and the thermal dose calibration to an operator, and allow the operator to operate the MRI-guided hyperthermia treatment. The frontend platform 130 comprises a graphic user interface (GUI) 132 and a controller 134. The GUI 132 displays the consecutive real-time visualization images and the thermal dose calibration to the operator. Referring to the real-time visualization images and the thermal dose calibration, the operator inputs a value (or a correction value) of thermal dose by the GUI 132 during the hyperthermia treatment. In one embodiment, the frontend platform 130 further comprises an input device, e.g., a mouse, a keyboard, a keypad, a touch screen, etc., via which the value of thermal dose may be inputted. The controller 134 receives and sends the value of thermal dose to a treatment unit 140 to control heating during the hyperthermia treatment. In one embodiment, the treatment unit 140 is a high intensity focused ultrasound (HIFU) unit, which generates focused ultrasonic energy for sonicating the ROT during the hyperthermia treatment. The value of thermal dose can be stored in the database 126 and used for training the predictive model. Besides, the predictive model could be pre-trained by prior knowledge, such as prior MRI images, prior thermograms, etc., obtained before the current hyperthermia treatment so that accuracy and success of the hyperthermia treatment can be increased.

The present invention provides a live-feedback system that utilizes GPU, computation and a database. In one example, the GPU is an on-site GPU. The computation and database may be cloud-based. In another example, the GPU is an HTIP-GPU. A deep learning method is employed to monitor changes in a selected ROT while iteratively learning its rate of change with respect to image features and sensory information. Accumulated in local and/or cloud-based database, this classified information can be called for predictive measures and as a mean to calibrate the thermal energy in treating neighboring and/or the remainder of an ROT. Aided by the high-performance of the GPU to offer predictive engagement of hyperthermia during the treatment, the side effects of under- or over-treatment can be minimized.

Platform Design

The present invention provide an operator or an operation team with a frontend platform, equipped with real-time visualization during the process of hyperthermia treatment, while performing an advanced machine learning-aided analysis to extract information from the MRI images and sensory data in the backend platform.

Figure 2:
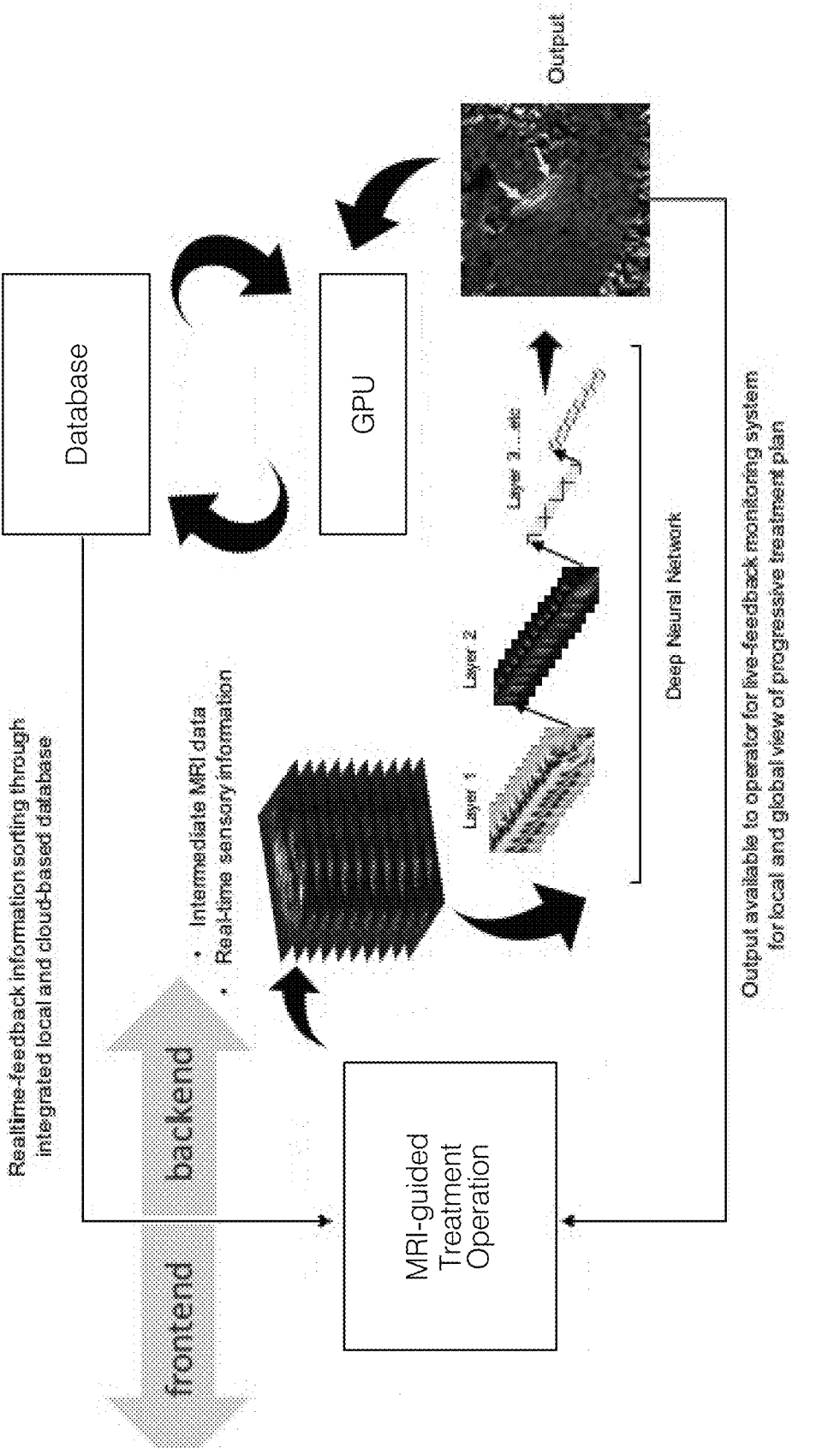
FIG. 2 is a schematic diagram showing MR imaging with AI-aided predictive feedback to guide hyperthermia treatment according to one embodiment of the present invention.
Figure 3:
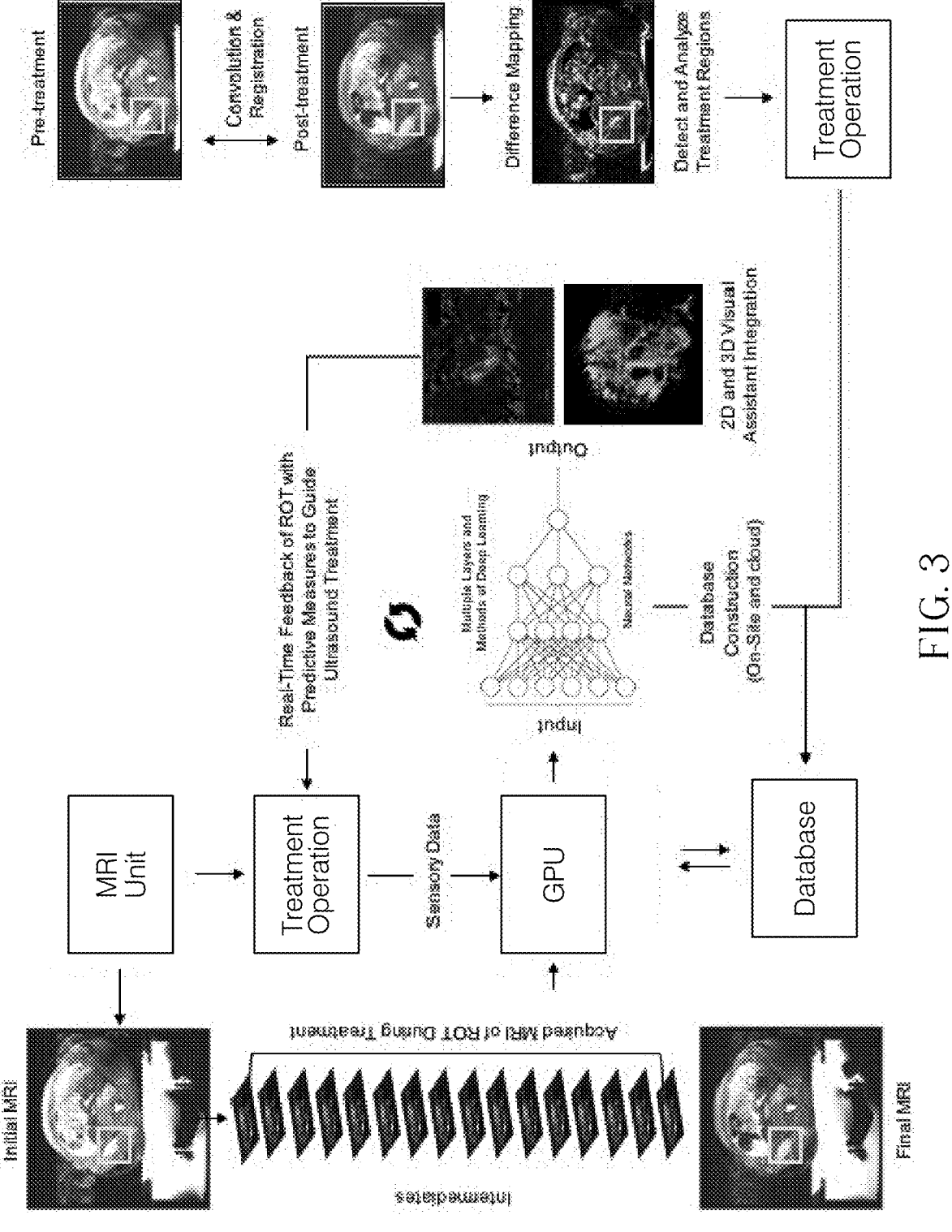
FIG. 3 is a schematic diagram showing AI-aided progressive treatment with predictive guidance and real-time feedback according to one embodiment of the present invention.

FIG. 2 is a schematic diagram showing MR imaging with AI-aided predictive feedback to guide hyperthermia treatment according to one embodiment of the present invention. FIG. 3 is a schematic diagram showing AI-aided progressive treatment with predictive guidance and real-time feedback according to one embodiment of the present invention.

1. Artificial Neural Networks Over Consecutive Hyperthermia Imaging

Image analysis is implemented to process and characterize thousands of images. Together with sophisticated image segmentation methods, the extracted features, such as size, shape and texture, of an ROT are used for characterization of each set of images. Additionally, machine learning is utilized to extract features of each ROT through, for instance, pre-trained convolutional and/or other artificial neural networks (ANN). Achievement of such meta-analysis requires advanced GPU performance for efficiency and precision of feature detection and predictive model training. In medical imaging, accurate diagnostic, analysis and treatment relies on improvements in image visualization and interpretation; thus, GPU-mediated image processing is critical for the development of machine learning-aided on-site and/or cloud-based analysis.

2. Machine Learning and Archiving

Referring to FIG. 3, the collected MRI images and sensory data during treatment, pre-treatment and post-treatment are utilized to construct a database or databases, which can be accessed locally and remotely. In one example, the database is constructed by cloud technology. The database is used to build a predictive model to guide the patient treatment. It is believed that data from hundreds of subjects and cases will be needed to make the initial predictive model accurate. Accuracy can be continuously increased with incremental machine learning methods to train the model during its usage. Pre-trained ANN can be employed to extract features from ROTs. High dimensional feature data including ANN-extracted image features and sensory data is further processed to lower dimensional data using non-linear dimensionality reduction methods by, for example, a deep autoencoder. The lower dimensional data is better suited for unsupervised learning methods used to cluster the data and detect anomaly events. Using data clustering and event detection, a supervised model is built to classify tumorous lesions and guide the hyperthermia treatment. This information can later be recalled from a global database and used as a reference for identification of similar ROTs.

3. Real-Time MRI Temperature Mapping

A real-time MRI temperature mapping has been developed using undersampled radial MRI sequences with iterative image reconstruction by regularized nonlinear inversion, a technique known as NLINV. Technological advances in accurate temperature mapping, using techniques of water/proton chemical shift measurements or proton resonance frequency, has made real-time monitoring of thermal dose accumulation possible. Prior to implementation of MRI in hyperthermia treatment, monitoring of local temperature deviation posed a challenge at tissue level. The energy deposition and calculation of thermal dose necessary to induce cell death was obstructed by temperature fluctuations caused by physiological actives and blood flow surrounding the tumor tissue, resulting in inaccurate heat conduction. The image-based temperature mapping has not been used for in vivo studies; it has been fully tested in vitro with high temporal resolution. Implementation of this method during hyperthermia would require dynamic temperature mapping; this can be achieved by the on-site GPU.

Interface Design

In the existing hyperthermia treatment, sonication thermal transduction can only be achieved solely based on the visual monitoring of the tumor tissue by the operator, who determines the thermal dose for treatment. Referring to FIG. 2, as indicated with the added interface, a real-time feedback thermal monitoring of an ROT or ROTs by 3D visualization to assess instant treatment planning can offer significant improvements. Machine learning during treatment is applied to enable predictive analysis of the ROT or ROTs and instant thermal dose calibration for the need of nearby treatments. Based on the images acquired in the backend, the present invention can construct a database utilized by a progressive machine learning analysis to guide the ROT profiling in correlation with the progressive treatment thermograms. This information can readily be available to the operator in the frontend.

Referring to FIG. 3, during each treatment, the intermediate MRI images along with any sensory data (such as regional temperature and thermal dose) are sent to the on-site HTIP-GPU, which processes the images and through a series of neural networks, pools ROT features for a predictive and/or suggestive guidance to the operator. Based on progressive machine learning and an integrated on-site database, the frontend GUI, available to the hyperthermia operator, will suggest predictive treatment to help avoid under- or over-treatment. Then, based on the information, the operator can make a decision and proceed with the hyperthermia treatment.

1. Visualization and Interpretation

Figure 4:
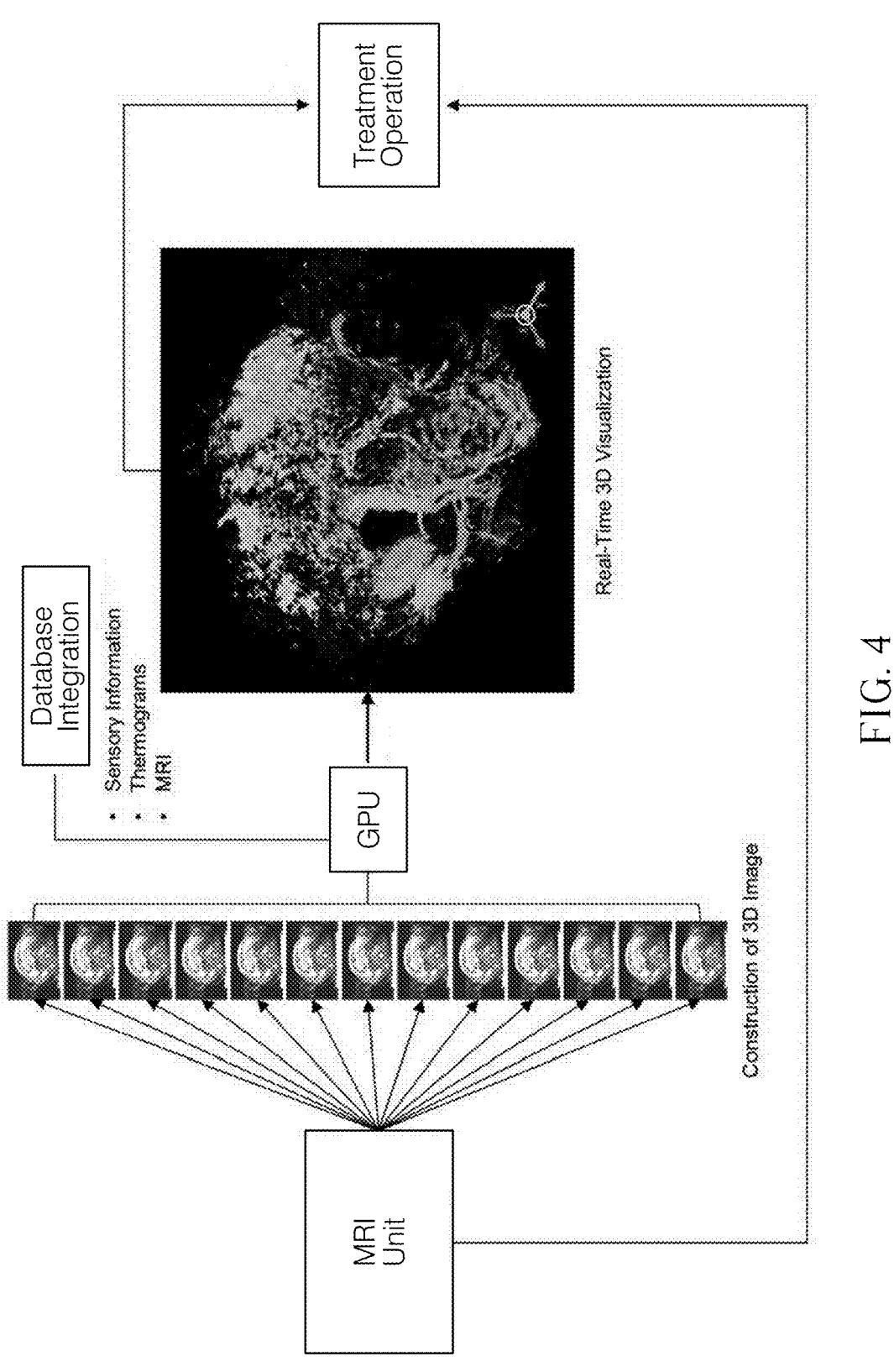
FIG. 4 is a schematic diagram showing real-time 3D visualization of treatment region according to one embodiment of the present invention.

The dimensionality of the data should be taken into close consideration. While the 2D image analysis on the axial, coronal, and sagittal images provides a map of the ROT, an integrated dimensionality of 2D/3D data mining would expand the scope of the analysis and medical applications towards image-guided cancer treatment. The full utilization of image-guided information allows for a more accurate identification and localization of the therapeutic target and surrounding healthy tissue. In addition, the GUI can provide real-time visualization images that can be in 2D and/or 3D to provide visual assistance during the hyperthermia treatment, as shown in FIG. 4. Lastly, to put the hyperthermia in context of the large areas of MRI-body scan, the pre-treatment and post-treatment images are aligned, and registration and convolution image processing methods are used. A difference map is generated for examination and analysis of the ROT. All together, this integrated real-time feedback system can provide the operator with enhanced treatment tools and reduce human errors during the treatment.

2. Predictive Hyperthermia Treatment

Figure 5:
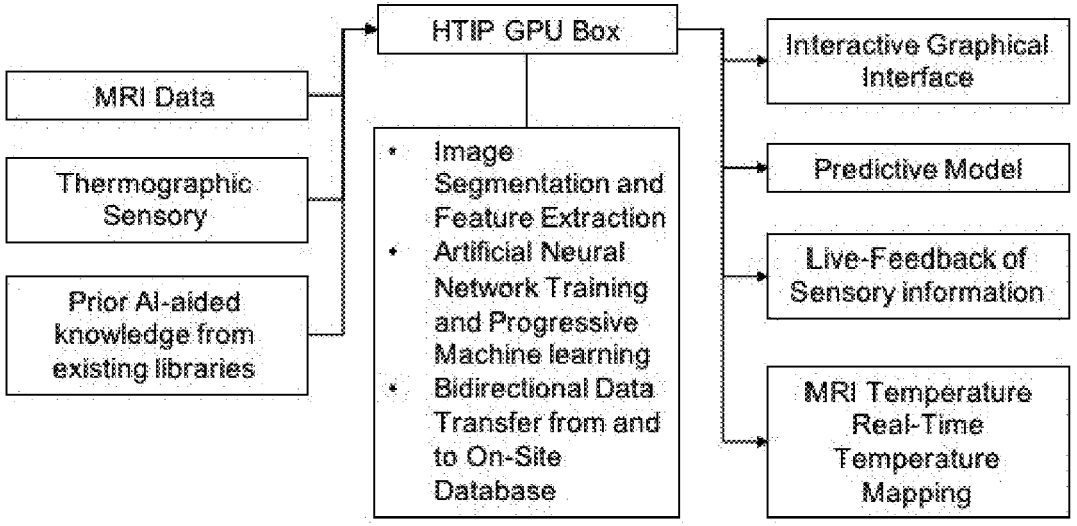
FIG. 5 is a process flow diagram showing a method of performing MRI-guided hyperthermia treatment according to one embodiment of the present invention.

FIG. 5 is a process flow diagram showing a method of performing MRI-guided hyperthermia treatment according to one embodiment of the present invention. To enhance the progressive machine learning, the present invention provides a bidirectional system that allows the operator to receive alerts from the machine learning of treatment images and send feedback to increase the accuracy of prediction during subsequent treatments. A semi-supervised frontend will be provided to overcome the variables of cumulative heating rates raised by the heterogeneity nature of tumor-tissues ratio and/or the abundance of running through blood vessels. Moreover, the operator can benefit from the virtual reality modeling to allow feedbacks on the fly with interactive vector-graphic feedbacks. By a simple click (or even touch-screen), the operator can: (1) move the volume in 3D space, and (2) click, zoom-in, and highlight the ROT. During the hyperthermia treatment session, the frontend, visible to the operator, displays an interactive interface with real-time 3D visualization of the ROT. As a part of the integrated live-feedback, the operator is provided with sensory information, such as temperature measurements and thermal dose, along with predictive deep-learning aided treatment alerts. Based on a deep-learning approach, a loopback system recalls suggestive information and provides the operator with instant information to control the on-going session of hyperthermia treatment.

Figure 6:
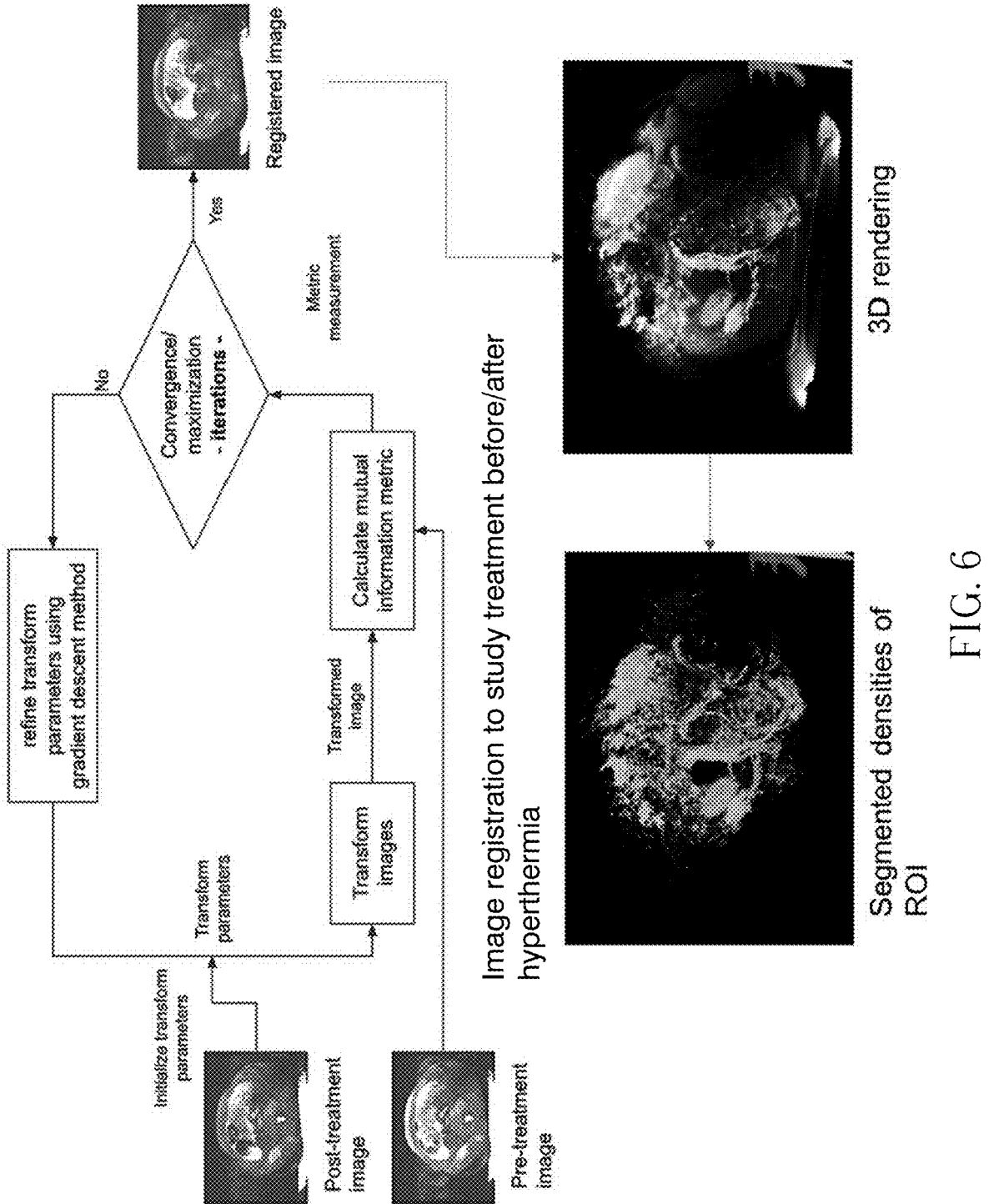
FIG. 6 is a schematic diagram showing a process of image registration according to one embodiment of the present invention.

FIG. 6 is a schematic diagram showing a process of image registration, which is used to study treatment before/after hyperthermia, according to one embodiment of the present invention. In order to track the progress of treatment, a set of MRI images of pre-treatment and post-treatment are captured. Because the time points between pre- and post-treatment MRI imaging sessions are different, computational means are necessary to calculate image components to achieve proper alignment and registration. In this way, images are transformed and mutual information is measured into a matrix, which is then maximized, normalized, and converged. This process is subject to improvement which is done through an iterative cycle of refinement. This task can be best achieved through neural network training (under the umbrella of artificial intelligence). For it is only after this registration that a proper 3D rendering is achieved and segmentation of the regions of interest (ROI) can be performed.

Figure 7:
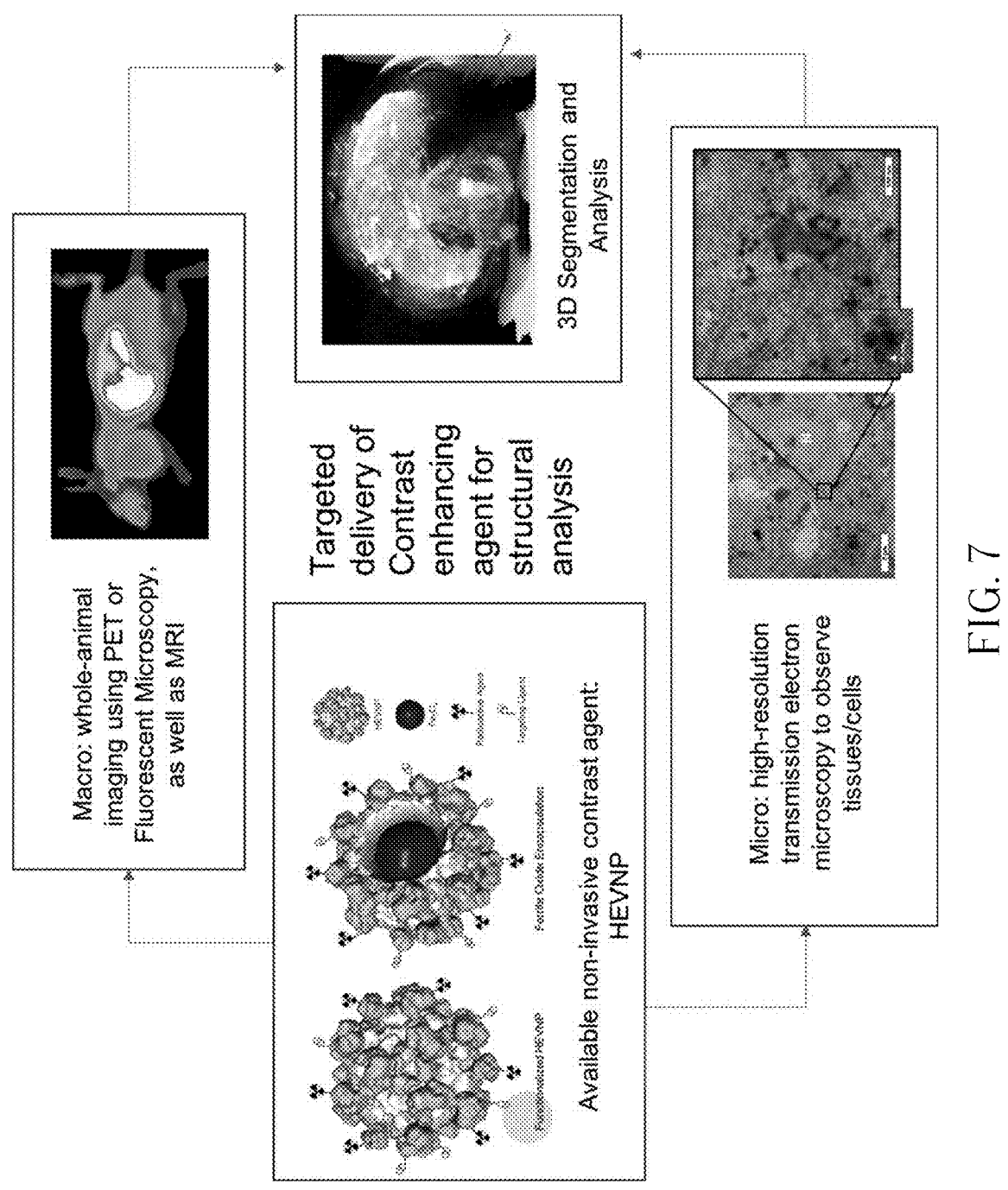
FIG. 7 is a schematic diagram showing segmentation and analysis of images according to one embodiment of the present invention.

FIG. 7 is a schematic diagram showing segmentation and analysis of images according to one embodiment of the present invention. Segmentation and analysis of images is often the most important task in data analysis and an important factor in the decision-making process for medical procedures. The search of regions of interest and segmentation of treated vs. untreated regions of a tumor can be simplified by the introduction of a contrast agent. Here, the hepatitis e nanoparticles (HEVNP) can be employed as a contrast agent with the capacity to display PET and fluorescent agents on its surface (which can be used for larger views and whole-body distribution analysis) or even at the cellular level while carrying electron-dense metals, such as ferrite oxide. Together, with HEVNP's targeting capacity, a specific region (i.e. tumor) of the body can be accurately targeted, imaged, and analyzed.

The features of the present invention are as follows:

Prior knowledge, for example, from previous thermo-grams and/or MRI images is used to train advanced artificial intelligence (AI) neural networks.

On-site high throughput data mining via a GPU is used.

A HTIP-GPU is used for measuring features such as morphological and textural components of all images to build a self-trained integrated system.

An image processing tool is used to calculate mutual information metrics between pre- and post-treatment MRI for hyperthermia treatment evaluation.

Real-time, consecutive MRI mapping associated with the predictive assessments of temperature is used.

Real-time 3D visualization is used to assist an operator during hyperthermia treatment session.

Prior knowledge is used for building a predictive model to provide interactive feedback to the operator. Suggestions can be made to stop, slow down, or speed up the heating.

Industrial interface programming is used to send and receive data to and from hardware.

Machine learning-aided data mining is used to provide feedbacks of parametric data for operative graphical user interface.

Virtual reality modeling is used to provide an interactive vector graphic interface to manipulate visual data in 3D.

Although the foregoing embodiments have been described in some detail for purposes of clarity of understanding, it will be apparent that certain changes and modifications may be practiced within the scope of the appended claims. It should be noted that there are many alternative ways of implementing the methods and structures of the present embodiments. Accordingly, the present embodiments are to be considered as illustrative and not restrictive, and the present invention is not to be limited to the details given herein.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the foregoing processes may be changed.

The subject matter of the present disclosure includes all novel and nonobvious combinations and sub-combinations of the various processes and configurations, and other features, functions, acts, and/or properties disclosed herein, as well as any and all equivalents thereof.

What is claimed is:

1. A system for performing MRI-guided hyperthermia treatment, comprising:

a magnetic resonance imaging (MRI) unit, configured to acquire MRI images from an imaging zone before, during and after a hyperthermia treatment, wherein the imaging zone includes a region of treatment (ROT) that are indicated by a contrast agent using hepatitis e nanoparticles (HEVNP);

a backend platform, comprising:

a graphic processing unit (GPU), configured to receive and process the MRI images from the MRI unit and sensory data, and detect features of the ROT for the MRI images;

a computing unit, configured to implement machine learning-aided analysis, wherein the machine learning-aided analysis extracts information from the features of the ROT and the sensory data to train a predictive model, and the predictive model generates, based on the MRI images and the sensory data, consecutive real-time visualization images of the ROT and thermal dose calibration during the hyperthermia treatment; and a database, configured to store the MRI images, the sensory data, the real-time visualization images and the thermal dose calibration; and a frontend platform, configured to display the consecutive real-time visualization images and the thermal dose calibration to an operator, and allow the operator to operate the MRI-guided hyperthermia treatment, the frontend platform comprising:

a graphic user interface (GUI), configured to display the consecutive real-time visualization images and the thermal dose calibration; and a controller, configured to receive a value of thermal dose inputted by the operator during the hyperthermia treatment, and send the value of thermal dose to a treatment unit to control heating during the hyperthermia treatment, wherein the sensory data is selected from the group consisting of regional temperature, thermal dose and biological effect;

wherein the features of the ROT includes textural components and size of the ROT;

wherein the GPU comprises a high-throughput image processing GPU (HTIP-GPU), the processing of the MRI images and sensory data is performed by the HTIP-GPU;

wherein the consecutive real-time visualization images comprise consecutive 3D real-time images.

2. The system of claim 1, the treatment unit comprises a high intensity focused ultrasound (HIFU) unit, which generates focused ultrasonic energy for sonicating the ROT during the hyperthermia treatment.

3. The system of claim 1, wherein the database is further configured to store the value of thermal dose inputted by the operator.

4. The system of claim 1, wherein the predictive model had been pre-trained by prior MRI images and/or prior thermograms obtained before the hyperthermia treatment.

5. The system of claim 4, wherein the predictive model is further trained by the value of thermal dose inputted by the operator.

6. The system of claim 1, wherein the features of the ROT includes morphological components.

7. The system of claim 6, wherein the features of the ROT are selected from the group consisting of shape, texture, and a combination thereof.

8. A method for performing MRI-guided hyperthermia treatment, comprising:

acquiring MRI images from an imaging zone before, during and after a hyperthermia treatment, wherein the imaging zone includes a region of treatment (ROT) that are indicated by a contrast agent using hepatitis e nanoparticles (HEVNP);

processing the MRI images and sensory data;

detecting features of the ROT for the MRI images;

extracting, by machine learning-aided analysis, information from the features of the ROT and the sensory data to train a predictive model;

generating, by the predictive model, consecutive real-time visualization images of the ROT and thermal dose calibration during the hyperthermia treatment, based on the MRI images and the sensory data;

displaying the consecutive real-time visualization images and the thermal dose calibration to an operator; and sending a value of thermal dose inputted by the operator to a treatment unit during the hyperthermia treatment, to control heating during the hyperthermia treatment, wherein the sensory data is selected from the group consisting of regional temperature, thermal dose and biological effect;

wherein the features of the ROT includes textural components and size of the ROT;

wherein the processing the MRI images and sensory data is performed by an HTIP-GPU;

wherein the consecutive real-time visualization images comprise consecutive 3D real-time images;

wherein the displaying the consecutive real-time visualization images comprises displaying consecutive 3D real-time visualization images.

9. The method of claim 8, further comprising:

pre-training, prior to the hyperthermia treatment, the predictive model by prior MRI images and/or prior thermograms obtained before the hyperthermia treatment.

10. The method of claim 8, the treatment unit comprises an HIFU unit, which generates focused ultrasonic energy for sonicating the ROT during the hyperthermia treatment.

11. The method of claim 8, wherein the detecting features of the ROT for the MRI images is performed by an HTIP-GPU.

12. The method of claim 8, wherein the features of the ROT includes morphological components.

13. The method of claim 8, further comprising:

storing the MRI images, the sensory data, the consecutive real-time visualization images and the thermal dose calibration.

14. The method of claim 13, further comprising:

storing the value of thermal dose inputted by the operator.

* * * * *